United States Patent
Ito

(10) Patent No.: US 9,517,155 B2
(45) Date of Patent: Dec. 13, 2016

(54) INCURVATED-NAILS AND INGROWN-NAILS CORRECTING DEVICE THAT USES A MAGNETIC FORCE

(71) Applicant: MEDICAL CORPORATION ITO DERMATOLOGY CLINIC, Tokyo (JP)

(72) Inventor: Haruo Ito, Tokyo (JP)

(73) Assignee: MEDICAL CORPORATION ITO DERMATOLOGY CLINIC, Tokyo (JP)

( * ) Notice: Subject to any disclaimer, the term of this patent is extended or adjusted under 35 U.S.C. 154(b) by 167 days.

(21) Appl. No.: 14/300,605

(22) Filed: Jun. 10, 2014

(65) Prior Publication Data
US 2015/0351948 A1    Dec. 10, 2015

(51) Int. Cl.
*A61F 5/11*    (2006.01)
(52) U.S. Cl.
CPC ...................... *A61F 5/11* (2013.01)
(58) Field of Classification Search
CPC ................ A61F 2013/00353; A61F 5/11
USPC ..................................... 602/30–31
See application file for complete search history.

(56) References Cited

U.S. PATENT DOCUMENTS

2009/0048551 A1 *  2/2009  Liberson ................. A61F 5/11
                                                            602/31

FOREIGN PATENT DOCUMENTS

| JP | 5311320 | | 7/2013 | |
| JP | 5311320 B1 | * | 10/2013 | |
| JP | 2013-230290 A | * | 11/2013 | ............... A61F 5/11 |

* cited by examiner

*Primary Examiner* — Victoria J Hicks
*Assistant Examiner* — Camtu Nguyen
(74) *Attorney, Agent, or Firm* — Greer, Burns & Crain, Ltd.

(57) ABSTRACT

Provided is an incurvated-nails and ingrown-nails correcting device that uses a magnetic force and that is capable of adjusting the space between a magnet and a magnetic sheet that is placed on a nail. The subject device includes a magnetic sheet that is placed on a nail; the device's main part that includes a body that is attached to the magnetic sheet by using an adhesive agent or by using the magnetic force of the magnet, an arm that extends outward from the body, a head that is arranged at the edge of the arm, and a joint by which the arm is rotatably connected to the body and by which the head is rotatably connected to the arm; and a magnet mounted on the head.

10 Claims, 3 Drawing Sheets

INCURVATED-NAILS AND INGROWN-NAILS CORRECTING DEVICE THAT USES A MAGNETIC FORCE

TECHNICAL FIELD

This invention relates to an incurvated-nails and ingrown-nails correcting device that uses a magnetic force, and more particularly to such a correcting device that is capable of adjusting the space between a magnet and a magnetic sheet that is placed on a fingernail or toenail, so that the fingernail or toe nail can be lifted slightly from the underlying skin of the finger or toe (hereinafter "lifted slightly").

BACKGROUND

Corrective treatment of nails that are incurvated or ingrown has required a medical doctor's expert knowledge and special techniques, and has caused a patient to experience pain while treatment is being provided. Furthermore, it has not been possible to provide corrective treatment to a small fingernail or toenail such as the nail of a person's little finger (i.e., the last finger as counted from the thumb) or little toe (i.e., the last toe as counted from the big toe).

The ingrown-nails correcting device disclosed in Patent Document 1 is made effective by using a magnet to attach the device to, and to fix it on, a nail plate. But that device is not capable of adjusting the position of its magnet according to the shape of the nail on which the device is used. Accordingly, the inventor of the current invention proposes a device that can correct incurvated nails and ingrown nails and that can be easily fitted on a finger or toe, that does not cause pain to a patient while the correcting device is fitted on a fingernail or toenail, and that can be maintained stably fitted on the fingernail or toenail while the patient performs his or her daily activities.

The device in Patent Document 1 is not capable of adjusting the position of the magnet according to the conditions of a fingernail or toenail. Because the magnet of the device in Patent Document 1 is merely horizontally placed on a nail plate's surface, the left and right sides of the magnet, which is straight, often do not come close enough to the left and right sides of the nail, which are curled downward, and therefore the magnetic force of the magnet cannot effectively work on the left and right sides of the nail. Accordingly, there is desired a correcting device whose magnet can be tilted so that the edge of the magnet can be brought closer to the sides of a nail.

PRIOR-ART DOCUMENT

Patent Document

Patent Document 1: JP-T-2009-531080

SUMMARY

The objective of the current invention is to provide an incurvated-nails and ingrown-nails correcting device that uses a magnetic force that is capable of adjusting the space between a magnet and a magnetic sheet that is placed on the fingernail or toenail, so that the fingernail or toe nail can be lifted slightly.

Means of Achieving the Objective

An incurvated-nails and ingrown-nails correcting device that uses a magnetic force according to the current invention (hereinafter "the current nail-correcting device") comprises (1) a magnetic sheet that is placed on a nail; (2) the device's main part that comprises (a) a body that is attached to the magnetic sheet by using an adhesive agent or by using the magnetic force of a magnet, (b) an arm that extends outward from said body, (c) a head that is arranged at the edge of said arm on said arm's side that is not attached to the body, and (d) a joint, by which the arm is rotatably connected to said body, and by which the head is rotatably connected to the arm respectively; and (3) a magnet that is mounted on the head. Said body comprises a central part and a side part, and a joint, by which said side part is rotatably connected to said central part, is provided between said central part and said side part.

Advantageous Effects

The current nail-correcting device is provided with a joint by which an arm is rotatably connected to a body and by which a head is rotatably connected to the arm, and therefore the current nail-correcting device is capable of adjusting the space between a magnet that is mounted on the device's head and a magnetic sheet that is placed on a fingernail or toenail. That is, the current nail-correcting device can place the magnet, which causes the fingernail or toenail to be lifted slightly, in such a way as to maintain a small distance between the magnet and the fingernail or toenail, according to the shape of the nail, whereby the current nail-correcting device can provide highly effective corrective treatment of incurvated nails and ingrown nails. Also, it is not necessary for a patient to insert a finger or toe into the correcting device's main part; it is sufficient just to dispose the device's main part on the nail of a finger or a toe, which is convenient for the patient, enabling the patient to feel comfortable when using the device. Moreover, the arm and the head can be tilted so that a magnetic force can work directly on the magnetic sheet that is placed on the nail, while keeping stable the position of the device's arm and the head. In addition, the current nail-correcting device can provide the following advantageous effects. The device's main part is attached to a magnetic sheet that is placed on a nail by using an adhesive agent or by the magnetic force of a magnet, and therefore neither high-level techniques nor special knowledge is required for using the current nail-correcting device. Accordingly, the current nail-correcting device can be used if a nail is thin and weak, or is thick, or is deformed, or is inflamed due to a secondary infection, by which the patient feels pain in the area of the nail. Because the current nail-correcting device causes a magnetic sheet that is placed on a nail to be lifted slightly by the magnetic force of a magnet, the nail can be lifted without causing pain to the patient. The device's main part does not move from its original position, but stably remains in that original position. Because the device's arms are extended outward in the left and right directions from the device's body, and heads on which a magnet is mounted are arranged on the arms, the current nail-correcting device can effectively cause a wide area of the nail to be lifted slightly in the right-left direction and front-back direction of the nail plate. The current device can be used on a nail without any surgical procedure, and therefore the current device can be used on a patient who has an infection, such as paronychia or nail ringworm, severe diabetes, or a blood-flow disorder. The current device can also be used on a person who is allergic to metal, even if the device is made of a metal instead of a resin, because the current device's main part does not directly contact the skin. In addition, it is not necessary for a patient to remove the device while taking a bath or exercising, and therefore, due to the patient's uninterrupted use of the correcting device, the effect of the treatment is enhanced.

In addition, the aforementioned body is configured so as to include a central part and a side part, in which the side part is rotatably connected to the central part, and therefore even if the shape of a nail is curved, the body can be bent so as to be stably fitted on the nail.

BRIEF DESCRIPTIONS OF THE DRAWINGS

DETAILED DESCRIPTION

The nail-correcting device that uses a magnetic force according to the current invention will be described below with reference to the drawings.

EXAMPLES

Figure 1:
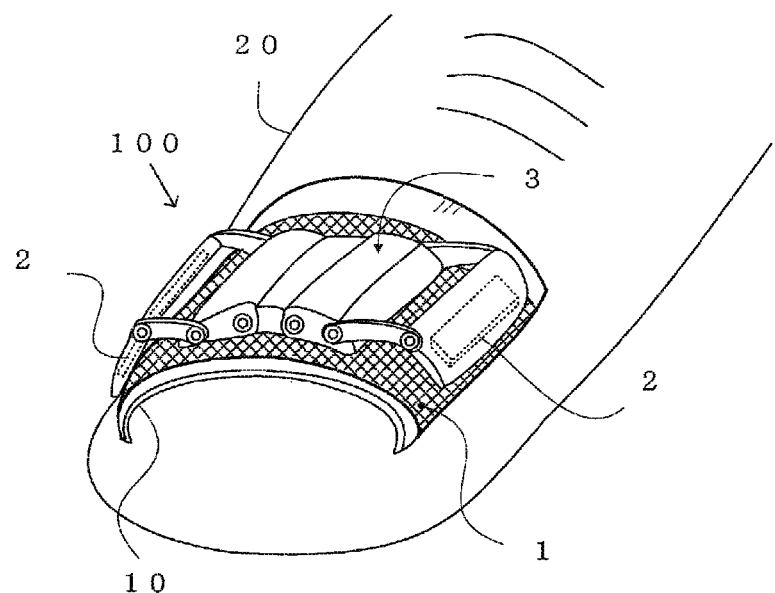
FIG. 1 is a perspective view of the incurvated-nails and ingrown-nails correcting device that uses a magnetic force according to the current invention.

FIG. 1 is a perspective view of a nail-correcting device that uses a magnetic force 100 according to the current invention. In FIG. 1, the nail-correcting device that uses a magnetic force 100 includes (1) a magnetic sheet 1 that is placed on a nail 10, (2) the device's main part 3 that is attached to the magnetic sheet 1 by using an adhesive agent or by using the magnetic force of a magnet 2, and (3) a magnet 2 that is provided to the device's main part 3 so as to cause the nail 10, on which the magnetic sheet 1 is placed, to be lifted slightly. The magnetic sheet 1 can be affixed to the nail 10 of a finger 20 by using an adhesive agent. Also, the device's main part 3 can be made of either a resin or a metal. Although in these examples magnets 2 are provided inside the device's main part 3, they can be provided outside of the device's main part 3.

Figure 2:
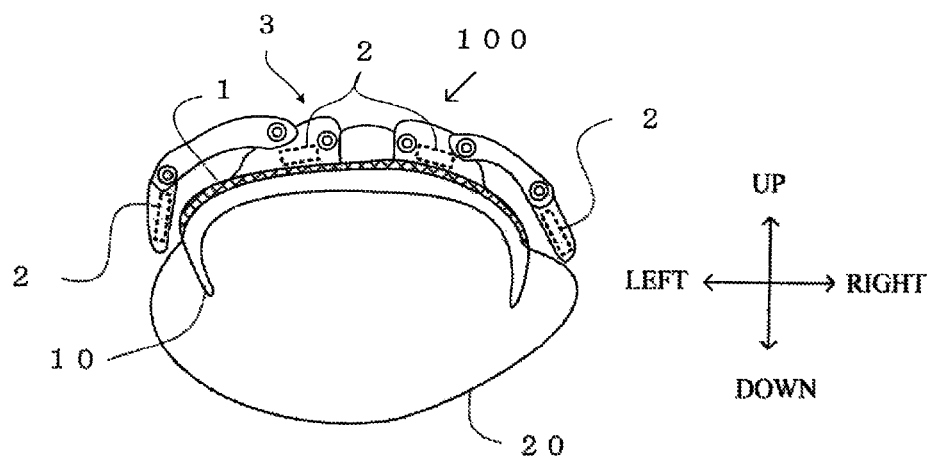
FIG. 2 is a front view of the nail-correcting device that uses a magnetic force shown in FIG. 1.

FIG. 2 is a front view of the nail-correcting device that uses a magnetic force 100 in FIG. 1. In FIG. 2, the magnets 2 provided on the left-side and right-side ends of the nail-correcting device that uses a magnetic force 100 cause the portions of the nail 10 corresponding to the left-side and right-side ends of the device, on which the magnetic sheet 1 is placed, to be lifted slightly. The positions of the magnets 2 on the left-side and right-side ends can be adjusted in such a way that neither of the magnets 2 contacts the magnetic sheet 1 while maintaining a predetermined space between the two magnets 2 and the magnetic sheet 1. The central part of the device's main part 3 is attached, to a sufficient width, to the magnetic sheet 1 by the magnetic force of the magnet 2. Therefore, for example, even if the left-side end of the correcting device is pushed downwards, the right-side end thereof does not rise. If the device's main part 3 is attached to the magnetic sheet 1 by using an adhesive agent instead of by using the magnetic force of the magnet 2, the adhesive force that joins the device's main part 3 with the magnetic sheet 1 can be increased further. Each magnet 2 on the left-side and right-side ends can be tilted so that the edge of each magnet 2 is appropriately close to the nail 10.

Figure 3:
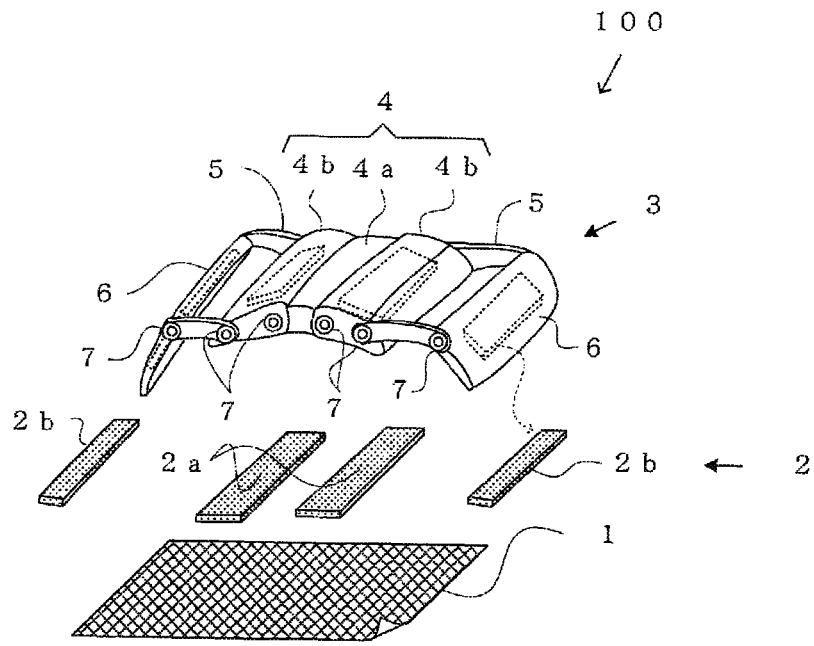
FIG. 3 is an exploded view showing the configuration of the nail-correcting device that uses a magnetic force shown in FIG. 1.

FIG. 3 is an exploded view showing the configuration of the nail-correcting device that uses a magnetic force 100 that is shown in FIG. 1. In FIG. 3, the device's main part 3 includes (1) a body 4 that is attached to the magnetic sheet 1 by using the magnetic three of the magnet 2a, which is embedded inside the body 4, (2) arms 5 that extend outward from the left end and right end, respectively, of said body 4, (3) a head 6 arranged at the edge of each of the arms 5, and (4) a joint 7, by which the arms 5 are rotatably connected to the body 4, and by which a head 6 is rotatably connected to each of the arms 5. A magnet 2b is embedded inside each head 6. The magnetic sheet 1 is cut according to the shape of the nail 10, so as to be placed on the nail 10. Joints 7 enable the arms 5 and the heads 6 to respectively rotate on one of the joints 7. The body 4 of this example includes a central part 4a and two side parts 4b that are arranged on the left side and right side, respectively, of the central part 4a. The side parts 4b are rotatably connected to the central part 4a by the joints 7. Each joint 7 includes (1) a hinge connection that uses a hinge pin, or (2) a recess and a projection fitting, which configuration allows the parts connected by the joints 7—i.e., the central part 4a, the side parts 4b, the arms 5, and the heads 6—to be rotatably connected. If the arms 5 and the heads 6 are suitably positioned after a predetermined rotation thereof is made, but the position of the arms 5 and the heads 6 cannot be stably kept at the predetermined position, the position of each arm 5 and each head 6 may be fixed by applying an adhesive agent on the joint 7.

Figure 4:
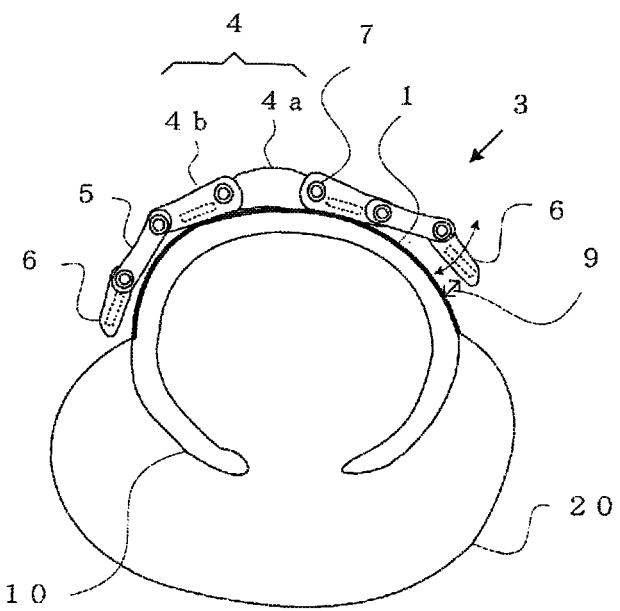
FIG. 4 shows an example in which the nail-correcting device that uses a magnetic force shown in FIG. 1 is used for correcting an incurvated nail.

FIG. 4 shows an example in which the nail-correcting device that uses a magnetic force 100 shown in FIG. 1 is being used to correct an incurvated nail. In FIG. 4, the nail-correcting device that uses a magnetic force is used to correct an incurvated nail 10 that curves around a finger or toe. The degree of rotation of the central part 4a and side parts 4b is increased according to the curvature of the nail.

Figure 5:
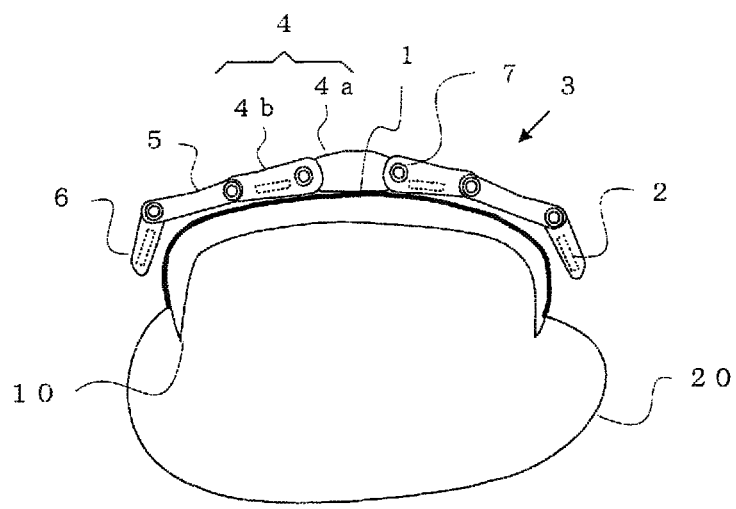
FIG. 5 shows an example in which the nail-correcting device that uses a magnetic force shown in FIG. 1 is used for correcting an ingrown nail.

FIG. 5 shows an example in which the nail-correcting device that uses a magnetic force 100 in FIG. 1 is used to correct an ingrown nail. In FIG. 5, the nail 10 has a shape such that its central part is relatively flat while the nail curves at almost right angles at the left-side and right-side ends of the nail, resulting in the ends biting into the skin of the finger or the toe. The degree of the rotation of the central part 4a and side parts 4b for an ingrown nail is smaller than that for an incurvated nail, depending on the shape of the nail.

Figure 6:
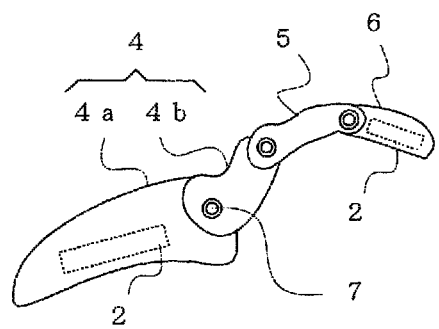
FIG. 6 shows another example of the nail-correcting device that uses a magnetic force according to the current invention.

FIG. 6 shows another example of the current nail-correcting device that uses a magnetic force. In FIG. 6, the body 4 includes a central part 4a and a side part 4b, and an arm 5 is arranged on only one side of the body 4 instead of on both sides of the body 4. The shape of this example is advantageous if the nail 10 has a shape that requires a correcting device with a head 6 that is arranged at only one side of the body 4.

Figure 7:
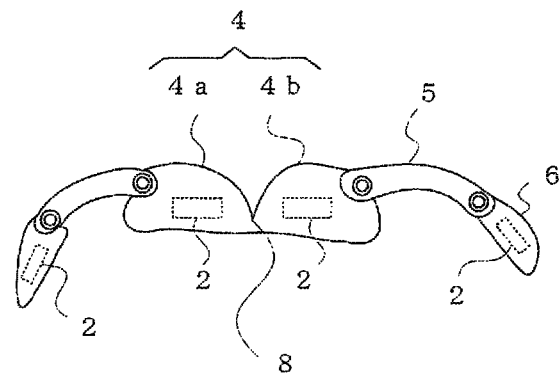
FIG. 7 shows an example of the nail-correcting device that uses a magnetic force in which a cut part is provided between the central part and the side part.

FIG. 7 shows an example of the current nail-correcting device that uses a magnetic force 100 in which a cut part is provided between a central part 4a and a side part 4b. In FIG.

7, the correcting device 100 is configured such that the central part 4a and the side part 4b have the same shape and form a cut part 8 between them. This configuration can also allow the body 4 to be bent according to the shape of the incurvated nail 10 in FIG. 4, and can also allow the body 4 to be almost flat, depending on the shape of the ingrown nail 10 in FIG. 5. In addition, it is preferable that the device's main part 3 is made of a resin, because the cut part 8 should be sufficiently flexible to be easy to bend.

A nail-correcting device that uses a magnetic force 100 of these examples is capable of adjusting the space between a nail 10 and the magnet 2 of a head 6, and is capable of maintaining the space at a preferred distance by fixing the position of the magnet 2 of the head 6 relative to the nail 10. Therefore, the magnet 2 of the head 6 is prevented from adhering to the magnetic sheet 1, and the magnet 2 also is prevented from being positioned too far from the magnetic sheet 1, so that the magnetic force that causes the nail 10 to be lifted slightly is provided effectively. A patient must wear the nail-correcting device that uses a magnetic force 100 for four months to six months.

The current invention is capable of adjusting the space between a nail and a magnet causing the nail to be lifted slightly, and is suitable for use as a nail-correcting device that uses a magnetic force.

LIST OF ALPHANUMERIC CHARACTERS USED

1 magnetic sheet
2 magnet
2a magnet embedded in a body
2b magnet embedded in a head
3 device's main part
4 body
4a central part
4b side part
5 arm
6 head
7 joint
8 cut part
9 space
10 nail
20 finger, toe
100 nail-correcting device that uses a magnetic force

The invention claimed is:

1. An incurvated-nails and ingrown-nails correcting device that uses a magnetic force, said device comprising:
   a magnetic sheet that is attachable on a nail;
   a main part of said device, comprising:
      a body that is attached to the magnetic sheet by using an adhesive agent or by using the magnetic force of a first magnet;
      an arm that extends outward from said body;
      a head that is arranged at an edge of said arm on said arm's side that is not attached to the body; and
      a first joint, by which the arm is rotatably connected to said body, and a second joint, by which the head is rotatably connected to the arm; and
   a second magnet that is mounted on the head;
   wherein
      the nail is able to be corrected by the magnetic force that is generated between the head and the magnetic sheet.

2. The device of claim 1, wherein the head is adjustable relative to the arm via the second joint for maintaining a predetermined space defined by the magnet sheet and the second magnet of the head.

3. The device of claim 1, wherein the body includes a central part and a side part.

4. The device of claim 3, further comprising a third joint disposed between the central part and the side part, such that the side part is rotatably connected to the central part.

5. The device of claim 3, wherein the side part includes a first portion and a second portion, such that the central part is sandwiched by the first and second portions of the side part.

6. The device of claim 3, wherein the first magnet is mounted to the side part.

7. The device of claim 3, wherein a cut part is disposed between the central part and the side part for allowing bending movement for the body.

8. The device of claim 1, wherein each joint includes a hinge connection that uses a hinge pin.

9. The device of claim 1, wherein each joint includes a recess and a projection fitting for allowing rotational movement for the corresponding joint.

10. The device of claim 1, wherein the device is made of at least partially with at least one of: a metal and a resin.

* * * * *